US012800584B2

(12) United States Patent
Brenner et al.

(10) Patent No.: US 12,800,584 B2
(45) Date of Patent: Nov. 17, 2026

(54) METHOD FOR IDENTIFYING COMPOUNDS INHIBITING AIF/CHCHD4 INTERACTION FOR THE TREATMENT OF CANCER

(71) Applicants: UNIVERSITÉ PARIS-SACLAY, Gif-sur-Yvette (FR); INSERM (INSTITUT NATIONAL DE LA SANTE ET DE LA RECHERCHE MEDICALE), Paris (FR); INSTITUT GUSTAVE ROUSSY, Villejuif (FR)

(72) Inventors: Catherine Brenner, Le Chesnay (FR); Nazanine Modjtahedi, Paris (FR)

(73) Assignees: UNIVERSITÉ PARIS-SACLAY, Gif-sur-Yvette (FR); INSERM (INSTITUT NATIONAL DE LA SANTÉ ET DE LA RECHERCHE MÉDICALE), Paris (FR); INSTITUT GUSTAVE ROUSSY, Villejuif (FR)

( * ) Notice: Subject to any disclaimer, the term of this patent is extended or adjusted under 35 U.S.C. 154(b) by 1053 days.

(21) Appl. No.: 17/802,550

(22) PCT Filed: Feb. 26, 2021

(86) PCT No.: PCT/FR2021/050335
§ 371 (c)(1),
(2) Date: Aug. 26, 2022

(87) PCT Pub. No.: WO2021/170963
PCT Pub. Date: Sep. 2, 2021

(65) Prior Publication Data
US 2023/0221321 A1 Jul. 13, 2023

(30) Foreign Application Priority Data
Feb. 28, 2020 (FR) ....................................... 2002003

(51) Int. Cl.
*G01N 33/575* (2026.01)
*A61K 49/14* (2006.01)
*C07K 14/47* (2006.01)
*C07K 19/00* (2006.01)
*G01N 33/68* (2006.01)

(52) U.S. Cl.
CPC ....... *G01N 33/575* (2026.01); *C07K 14/4747* (2013.01); *C07K 19/00* (2013.01); *G01N 33/68* (2013.01)

(58) Field of Classification Search
None
See application file for complete search history.

(56) References Cited

U.S. PATENT DOCUMENTS

2019/0330364 A1* 10/2019 Johnston ............ C07K 16/2896

FOREIGN PATENT DOCUMENTS

WO WO 2013/067036 5/2013
WO WO 2014/118296 8/2014

OTHER PUBLICATIONS

Thomas et al. (2019). Cancer and Metabolism. 16:7:7 (17 pages).*
Cekanova et al. (2014). Drug Design, Development and Therapy. 8:1911-1922.*
Bano, D. et al. "Apoptosis-Inducing Factor (AIF) in Physiology and Disease: The Tale of a Repented Natural Born Killer" *EBioMedicine*, Mar. 23, 2018, pp. 29-37, vol. 30.
Eglen, R. M. et al. "The Use of AlphaScreen Technology in HTS: Current Status" *Current Chemical Genomics*, 2008, pp. 2-10, vol. 1.
Hangen, E. et al. "Interaction between AIF and CHCHD4 Regulates Respiratory Chain Biogenesis" *Molecular Cell*, Jun. 18, 2015, pp. 1001-1014, vol. 58, No. 6.
Modjtahedi, N. et al. "Metabolic epistasis among apoptosis-inducing factor and the mitochondrial import factor CHCHD4" *Cell Cycle*, Sep. 1, 2015, pp. 2743-2747, vol. 14, Issue 17.
Rao, S. et al. "AIF-regulated oxidative phosphorylation supports lung cancer development" *Cell Research*, May 27, 2019, pp. 579-591, vol. 29, No. 7.
Reinhardt, C. et al. "AIF meets the CHCHD4/Mia40-dependent mitochondrial import pathway" *BBA—Molecular Basis of Disease*, Feb. 24, 2020, pp. 1-14, vol. 1866, No. 6.
Saunders, L. P. et al. "Identification of small-molecule inhibitors of autotaxin that inhibit melanoma cell migration and invasion" *Molecular Cancer Therapeutics*, Oct. 13, 2008, pp. 3352-3362, vol. 7, No. 10.
Thomas, L. W. et al. "CHCHD4 regulates a proliferation-EMT switch in tumour cells, through respiratory complex I mediated metabolism" *bioRxiv*, Jan. 7, 2019, pp. 1-29.
Written Opinion in International Application No. PCT/FR2021/050335, Jun. 24, 2021, pp. 1-11.

* cited by examiner

*Primary Examiner* — Christine J Saoud
*Assistant Examiner* — Jon M Lockard
(74) *Attorney, Agent, or Firm* — SALIWANCHIK, LLOYD & EISENSCHENK

(57) ABSTRACT

The invention relates to a method for identifying compounds useful for the treatment of cancer based on assessing the ability of the compound to modulate the interaction between the AIF protein and the CHCHD4 protein.

5 Claims, 2 Drawing Sheets

Specification includes a Sequence Listing.

METHOD FOR IDENTIFYING COMPOUNDS INHIBITING AIF/CHCHD4 INTERACTION FOR THE TREATMENT OF CANCER

CROSS-REFERENCE TO RELATED APPLICATION

This application is the U.S. national stage application of International Patent Application No. PCT/FR2021/050335, filed Feb. 26, 2021.

REFERENCE TO SEQUENCE LISTING

The Sequence Listing for this application is labeled "Seq-List.txt" which was created on Aug. 18, 2022 and is 11,570 bytes. The entire content of the sequence listing is incorporated herein by reference in its entirety.

TECHNICAL FIELD

The invention relates to a method for identifying compounds useful for the treatment of cancer, based on assessing the capacity of the compound to modulate the interaction between the AIF protein and the CHCHD4 protein.

TECHNOLOGICAL BACKGROUND

During the carcinogenesis process, the metabolism of cancer cells is reprogrammed so as to promote the growth of the tumor cells to improve their repair and invasion capacities and their resistance to anticancer treatments. Mitochondria are major participants in cell metabolism via, inter alia, their capacity to produce ATP, to produce various metabolites and macromolecules, to produce and detoxify reactive oxygen species and to modulate cell this death. For reason, targeting mitochondrial activity in order to affect the metabolism of cancer cells constitutes an approach of interest in the treatment of cancers. However, the mitochondrial molecular mechanisms capable of providing a therapeutic benefit still remain to be determined.

In order to function, the mitochondrion must import between 1500 and 2000 proteins encoded by the nuclear genome by virtue of particular protein machineries. Thus, AIF (Apoptosis Inducing Factor) and CHCHD4 (coiled-coil-helix-coiled-coil-helix domain containing 4) are two proteins expressed in the intermembrane space which, once linked together, form an import machinery for various proteins having cysteine motifs.

The AIF/CHCHD4 interaction has been described in the article Hangen et al. 2015 in vitro and in cellulo. In particular, this article demonstrates that the function of the AIF protein in the biogenesis of mitochondrial respiratory chain complexes is mediated by its physical and functional interaction with CHCHD4.

SUMMARY OF THE INVENTION

With the aim of identifying new compounds useful for the treatment of cancer, the inventors have developed an identification method based on assessing the capacity of a compound to inhibit the interaction between the AIF protein and the CHCHD4 protein. The hypothesis of the inventors is that a compound which inhibits formation of the AIF/CHCHD4 complex would be capable of affecting cancer cells, the survival and proliferation of which depend on the mitochondrial activity.

The method developed by the inventors has proved to be particularly effective since it has made it possible to identify compounds having anticancer properties. In addition, the present method has the advantage of being applicable to high-throughput screening, thus facilitating the identification of compounds potentially useful for the treatment of cancer.

One aspect of the invention thus relates to a method for identifying a compound potentially useful for the treatment of cancer, characterized in that it comprises assessing the capacity of said compound to inhibit the interaction between the AIF protein and the CHCHD4 protein, said compound being identified as potentially useful for the treatment of cancer if it inhibits said interaction.

In one particular embodiment, the method comprises:

(a) contacting the AIF protein and the CHCHD4 protein in the presence and in the absence of said compound;

(b) measuring the interaction between the AIF protein and the CHCHD4 protein, in the presence and in the absence of said compound; and (c) comparing the measurement of said interaction in the presence and in the absence of said compound;

said compound being identified as potentially useful for the treatment of cancer if the measurement of said interaction is lower in the presence of said compound than in the absence of said compound.

In one particular embodiment, the compound is identified as potentially useful for the treatment of cancer if it inhibits by at least 50%, 60%, 70%, 80%, or by at least 90%, the interaction between the AIF protein and the CHCHD4 protein.

The measurement of the interaction between the AIF protein and the CHCHD4 protein can be carried out by means of an amplified luminescent proximity homogeneous assay (ALPHA) or a surface plasmon resonance (SPR) assay. In addition, the method according to the invention may comprise the confirmation, in a nonhuman animal or cell model of cancer, of the anticancer properties of the compound identified.

In one particular embodiment, the method comprises:

(i) determining the capacity of said compound to inhibit the interaction between the AIF protein and the CHCHD4 protein, by means of an amplified luminescent proximity homogeneous assay (ALPHA);

(ii) determining the capacity of said compound to inhibit the interaction between the AIF protein and the CHCHD4 protein, by means of a surface plasmon resonance (SPR) assay; and (iii) confirming, in a nonhuman animal or cell model of cancer, the anticancer properties of the compound identified.

Another aspect of the invention relates to a kit for identifying a compound potentially useful for the treatment of cancer, characterized in that it comprises:

an AIF protein;

a CHCHD4 protein;

means suitable for measuring the interaction between the AIF protein and the CHCHD4 protein;

optionally, a buffer suitable for the experiment to measure said interaction; and optionally, a compound capable of inhibiting the interaction between the AIF protein and the CHCHD4 protein.

The means suitable for measuring the interaction between the AIF protein and the CHCHD4 protein can be means suitable for an amplified luminescent proximity homogeneous assay (ALPHA). In one particular embodiment, the buffer suitable for the experiment to measure the interaction between the AIF protein and the CHCHD4 protein comprises phosphate buffered saline (PBS) and bovine serum albumin (BSA). In one particular embodiment, said compound capable of inhibiting the interaction between the AIF protein and the CHCHD4 protein consists of the sequence of SEQ ID NO: 4 or any functional variant having at least 70%, 80%, 90%, or at least 99%, identity with the sequence of SEQ ID NO: 4.

DETAILED DESCRIPTION

1—Identification Method

Figure 1:
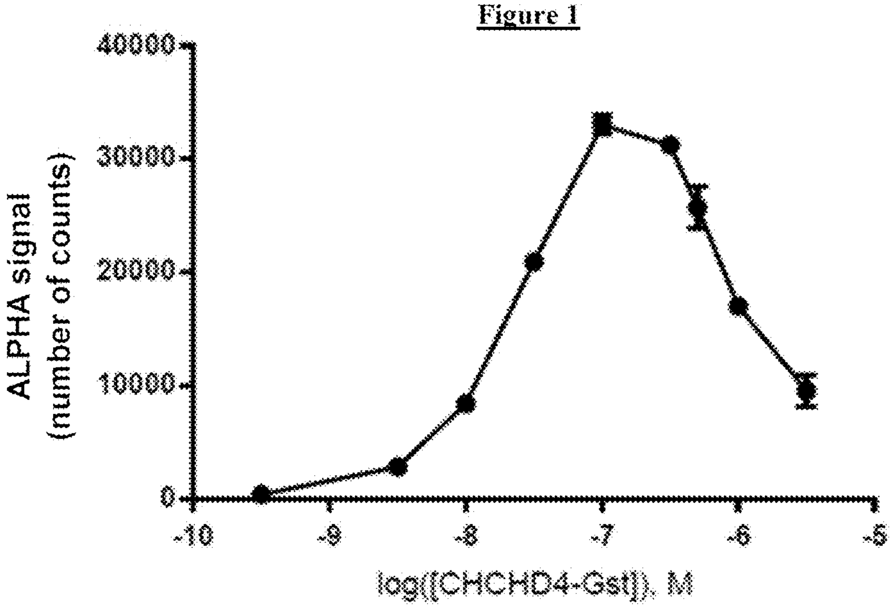
FIG. 1: AIF103-613 and CHCHD4 titration by Alphascreen. The titration of the CHCHD4 protein against the AIF103-613 protein using the ALPHAscreen technology results in a bell-shaped response called the Hook effect.

One aspect of the invention relates to a method for identifying a compound potentially useful for the treatment of cancer, characterized in that it comprises assessing the capacity of a compound to inhibit the interaction between the AIF protein and the CHCHD4 protein, said compound being identified as potentially useful for the treatment of cancer if it inhibits said interaction. One aspect of the invention relates in particular to a method for screening a compound library in order to identify a compound potentially useful for the treatment of cancer, characterized in that it comprises evaluating the capacity of the compounds of said compound library to inhibit the interaction between the AIF protein and the CHCHD4 protein, said compounds being identified as potentially useful for the treatment of cancer if they inhibit said interaction.

In one particular embodiment, the method according to the invention comprises:

(a) contacting the AIF protein and the CHCHD4 protein in the presence and in the absence of said compound;

(b) measuring the interaction between the AIF protein and the CHCHD4 protein, in the presence and in the absence of said compound; and (c) comparing the measurement of said interaction in the presence or in the absence of said compound;

said compound being identified as potentially useful for the treatment of cancer if the measurement of said interaction is lower in the presence of said compound than in the absence of said compound.

AIF and CHCHD4 Proteins

The physical and direct interaction of the AIF and CHCHD4 proteins was demonstrated in the article by Hangen et al., 2015.

The AIF (Apoptosis Inducing Factor) protein is a flavoprotein present in mitochondria and which promotes apoptosis when it is released from the mitochondrion. In the context of the present invention, the AIF protein may be of any origin, of animal preferably origin, in particular a mammal, more preferentially of human origin. In one particular embodiment, the AIF protein corresponds to the human natural AIF protein, the NCBI sequence reference of which is "NP 004199.1", or any functional variant thereof, such as AIF2 which is a specific brain isoform. In particular, the AIF protein according to the invention may correspond to the natural human polypeptide of sequence SEQ ID NO: 1, or any functional variant. The expression "functional variant" which refers to the AIF protein denotes any polypeptide derived from the structure of the AIF protein and which retains the capacity to bind to the CHCHD4 protein, in particular to the CHCHD4 protein of SEQ ID NO: 2. The functional variants may be natural or synthetic variants, such as fragments, mutants of deletants. Preferably, the functional variant of the AIF protein corresponds to a polypeptide having a sequence identity of at least 50%, 60%, 70%, 80%, 90%, or at least 95%, with the AIF protein of sequence SEQ ID NO: 1.

The CHCHD4 protein (also called mitochondrial intermembrane space import and assembly protein 40, or MIA40) is a protein which participates in protein import, in the mitochondrial intermembrane space. In the context of the present invention, the CHCHD4 protein may be of any origin, preferably of animal origin, in particular a mammal, more preferentially of human origin. In one particular embodiment, the CHCHD4 protein corresponds to the human natural CHCHD4 protein, the NCBI sequence reference of which is "NP 001091972.1". In particular, the CHCHD4 protein according to the invention may correspond to the natural human polypeptide of sequence SEQ ID NO: 2 or any functional variant. The expression "functional variant" referring to the CHCHD4 protein denotes any polypeptide derived from the structure of the CHCHD4 protein and which retains the capacity to bind to the AIF protein, in particular to the AIF protein of SEQ ID NO: 1. The functional variants may be natural or synthetic variants, such as fragments, mutants or deletants. Preferably, the functional variant of the CHCHD4 protein corresponds to a polypeptide having a sequence identity of at least 50%, 60%, 70%, 80%, 90%, or at least 95%, with the CHCHD4 protein of sequence SEQ ID NO: 2.

In one particular embodiment, the functional variant of the AIF protein is deleted or truncated compared to the AIF protein of SEQ ID NO: 1. In particular, the functional variant of the AIF protein may correspond to a polypeptide whose the transmembrane part of the AIF protein has been deleted. In one particular embodiment, the functional variant of the AIF protein corresponds to a polypeptide e SEQ ID NO: 3, or to a polypeptide having a sequence identity of at least 50%, 60%, 70%, 80%, 90%, or at least 95%, with the polypeptide of sequence SEQ ID NO: 3.

The AIF and CHCHD4 proteins can be modified, provided that this does not prevent the interaction between the two proteins. For example, for the needs of the measurement experiment of their interaction, the AIF and/or CHCHD4 proteins can be fused to a fragment used as a tag. Any conventional tag may be used, provided that it does not prevent the interaction between the two proteins. In particular, any tag suitable for an amplified luminescent homogeneous assay proximity (ALPHA) or for a surface plasmon resonance (SPR) assay can be used. More particularly, the AIF and/or CHCHD4 proteins can be fused to a Histidine tag corresponding to a motif consisting of several histidine residues, or to a GST tag corresponding to the glutathione-S-transferase protein.

Compound to be Tested

The compounds that may be identified by the method of the invention may be compounds of varied nature, structure and origin. The compounds that may be identified may in particular be biological, chemical, synthetic, etc., compounds. They may in particular be compounds of nucleic, peptide, lipid or carbohydrate nature. This may also involve libraries, in particular chemical libraries, protein, peptide, nucleic acid or natural substance libraries, etc.

Contacting the Compound to be Tested with the AIF and CHCHD4 Proteins

The compound to be tested can be brought into contact with the AIF protein and the CHCHD4 protein in any suitable support and in particular on a plate, in a tube or a flask, a membrane, etc. In particular, the contact can be carried out in a multiwell plate, thereby making it possible to perform numerous and varied assays in parallel. Among the typical supports are microtitration plates and more particularly 96-well or 384-well (or more) plates, which are easy to handle.

The amount (or the concentration) of compound to be tested can be adjusted by the user according to the type of compound, the duration of the incubation period, etc. In particular, the concentration of the compound to be tested may vary from 1 nM to 1 mM. It is of course possible to test other concentrations without departing from the present invention. Each compound can, furthermore, be tested in parallel, at various concentrations. Likewise, the amount (or concentration) of AIF and CHCHD4 proteins can vary and can be adjusted by the user. In particular, the concentration of AIF and CHCHD4 proteins is adjusted so as to allow optimal interaction between the two proteins, in the absence of the compound to be tested.

The contact between the proteins and the compound to be tested can be maintained for example between a few minutes and several hours or days, particularly between 30 minutes and 72 hours, more particularly between 1 and 5 hours.

The order of addition of the AIF protein, the CHCHD4 protein and the compound to be tested, when they are brought into contact, can be adjusted by those skilled in the art. In particular, the compound to be tested can be preincubated with the AIF protein for a certain period of time, before being brought into contact with the CHCHD4 protein. Alternatively, the compound to be tested can be preincubated with the CHCHD4 protein for a certain period of time, before being brought into contact with the AIF protein. The period of time during which the preincubation takes place with one or other of the proteins can be a few minutes, or several hours or days, more particularly between 5 and 60 minutes, more particularly between 5 and 30 minutes.

Measuring the Interaction of the AIF and CHCHD4 Proteins

The interaction of the AIF and CHCHD4 proteins, in the presence or in the absence of the compound to be tested, can be measured according to any technique known to those skilled in the art which makes it possible to measure or quantify the interaction between two proteins.

The term "interaction" means the pairing or the physico-chemical binding between the two proteins. The interaction between two proteins can result from covalent bonds and/or noncovalent bonds. Noncovalent bonds comprise in particular electrostatic, ionic, hydrogen and hydrophobic bonds, and also Van der Waals forces.

The method according to the invention comprises measuring the interaction of the AIF and CHCHD4 proteins, on the one hand in the absence of the compound to be tested, and on the other hand in the presence of the compound to be tested. The two measurements can be carried out consecutively or simultaneously. The two measurements of interaction, in the presence or in the absence of the compound to be tested, are subsequently compared. In one particular embodiment, the compound is identified as potentially useful for the treatment of cancer if it inhibits the interaction between the AIF protein and the CHCHD4 protein by at least 20%, 30%, 40%, 50%, 60%, 70%, 80%, or by at least 90%. Preferably, the compound is identified as potentially useful for the treatment of cancer if it inhibits the interaction between the AIF protein and the CHCHD4 protein by at least 508, 60%, 70%, 80%, or by at least 90%. In one particular embodiment, the compound is identified as potentially useful for the treatment of cancer if it inhibits the interaction between the AIF protein and the CHCHD4 protein by at least 50%.

The measurement of the interaction of the AIF and CHCHD4 proteins in the presence or in the absence of the compound to be tested can be carried out by means of any technique which makes it possible to measure or quantify the interaction between two proteins, for example by means of an amplified luminescent proximity homogeneous assay (ALPHA), a surface plasmon resonance (SPR) assay, a thermal shift assay (TSA) method, an immunoprecipitation method, an isothermal titration calorimetry (ITC) assay, a fluorescence resonance energy transfer (FRET) assay, a fluorescence polarization assay or an ELISA assay. In one particular embodiment, the measurement of the interaction of the AIF and CHCHD4 proteins is carried out by means of an ALPHA or SPR assay.

Preferably, the technique for measuring the interaction of the AIF and CHCHD4 proteins is applicable to high-throughput screening.

In one particular embodiment, the measurement of the interaction between the AIF protein and the CHCHD4 protein is carried out by means of an amplified luminescence proximity homogeneous assay (ALPHA). The ALPHA technology is a very sensitive technique based on the detection of chemiluminescence which makes it possible to screen a wide range of interactions and of biological activities and which is also suitable for high-throughput screening (see, for example, Eglen R M et al. The use of AlphaScreen technology in HTS: current status. Curr Chem Genomics. 2008; 1:2-10; Ullman E F et al. Luminescent oxygen channeling immunoassay: measurement of particle binding kinetics by chemiluminescence. Proc Natl Acad Sci USA. 1994; 91 (12): 5426-5430; Yasgar A et al. AlphaScreen-Based Assays: Ultra-High-Throughput Screening for Small-Molecule Inhibitors of Challenging Enzymes and Protein-Protein Interactions. Methods Mol Biol. 2016; 1439:77-98; Seethala and Prabhavathi, "Homogeneous Assays: AlphaScreen, Handbook of Drug Screening," Marcel Dekkar Pub. 2001, pp. 106-110).

The ALPHA technology, also known under the trade names AlphaScreen® and AlphaLISA®, makes it possible to measure the interaction of two molecules bioconjugated to donor beads and acceptor beads. The donor beads contain a photosensitive molecule, such as phthalocyanine, which converts ambient oxygen into singlet oxygen after excitation at 680 nm. The singlet oxygen can diffuse up to approximately 200 nm in solution. If an acceptor bead is within this distance, the energy is transferred from the singlet oxygen to thioxene derivatives in the acceptor bead, which results in an emission of light at 520-620 nm (AlphaScreen®) or at 615 nm (AlphaLISA®). If the donor bead is not in proximity to an acceptor bead, the singlet oxygen returns to the fundamental state and no luminescent signal is produced. In a protein/protein interaction assay, a protein is conjugated to the donor beads, and the other protein is conjugated to the acceptor beads. Thus, when the two proteins interact, the donor bead is brought into the proximity of the acceptor bead, and the excitation of the donor bead results in the emission of a quantifiable light signal on the part of the acceptor bead. The measurement of the light signal is carried out by means of a reader compatible with the ALPHA technology, such as the EnVision® or EnSpire® plate reader. In one particular embodiment, the measurement of the interaction is carried out by means of the AlphaScreen® assay.

The intensity of the light signal thus makes it possible to quantify the interaction of the proteins in a sample. Thus, the compound to be tested is identified as potentially useful for the treatment of cancer if the measurement of the light signal is lower in the presence of said compound than in the absence of said compound. In one particular embodiment, the compound is identified as potentially useful for the treatment of cancer if it inhibits the light signal measured in the absence of the compound to be tested by at least 208, 308, 40%, 50%, 60%, 70%, 80%, or by at least 90%. Preferably, the compound is identified as potentially useful for the treatment of cancer if it inhibits the light signal measured in the absence of the compound to be tested by at least 50%, 60%, 70%, 80%, or by at least 90%. In one particular embodiment, the compound is identified as potentially useful for the treatment of cancer if it inhibits the light signal measured in the absence of the compound to be tested by at least 50%.

In the context of the present invention, the AIF protein can be conjugated to the donor bead and the CHCHD4 protein to the acceptor bead, and vice versa: the AIF protein can be conjugated to the acceptor bead and the CHCHD4 protein to the donor bead. In one particular embodiment, the donor beads and the acceptor beads are covered with molecules or functional groups which allow them to be conjugated with one or the other of the AIF or CHCHD4 proteins.

The proteins can be fused to tags which allow them to be conjugated to the donor or acceptor beads. For example, the AIF protein or the CHCHD4 protein can be fused to a histidine tag allowing it to be conjugated to a nickel-covered bead, or a GST tag allowing it to be conjugated to a glutathione-covered bead.

Thus, according to one particular embodiment, the method comprises:

(a') contacting an AIF protein, a CHCHD4 protein, a donor bead and an acceptor bead, in the presence or in the absence of a candidate compound;

(b') exciting the donor bead at a given wavelength, preferably at a wavelength of approximately 680 nm;

(c') measuring the light signal emitted by the acceptor bead, the light signal preferably having a wavelength between 520 and 620 nm;

(d') comparing the measurement of the light signal in the presence and in the absence of the compound;

wherein the donor bead is capable of conjugating to the AIF protein and the acceptor bead to the CHCHD4 protein, or wherein the donor bead is capable of conjugating to the CHCHD4 protein and the acceptor bead to the AIF protein; said compound being identified as potentially useful for the treatment of cancer if the measurement of the light signal is lower in the presence of said compound than in the absence of said compound.

In another embodiment, the measurement of the interaction of the AIF and CHCHD4 proteins in the presence or in the absence of the compound to be tested is measured by means of a surface plasmon resonance (SPR) assay such as the Biacore® assay. During an SPR experiment, one of the two proteins is bound onto a surface (sensor chip), whereas the other is delivered onto the surface via a continuous stream of buffer by means of a microfluidic system. The interaction of the proteins is monitored by surface plasmon resonance, which detects the changes in mass at the level of the surface.

In one particular embodiment, the steps of contacting (a), of measuring the interaction (b), of comparing (c) of the method of the invention as described above can be repeated. In particular, steps (a), (b) and (c) can be repeated using, for each repetition, the same technique for measuring the interaction between the AIF and CHCHD4 proteins, or a different measurement technique. The advantage of the repetition of steps (a), (b) and (c) is to refine the screening method and to confirm the capacity of the compound to inhibit the interaction between the AIF and CHCHD4 proteins. For example, for each compound to be tested, steps (a), (b) and (c) can be carried out in duplicate, triplicate, quadruplicate or in quintuplicate.

In addition, steps (a), (b) and (c) of the method of the invention can be repeated using the same technique for measuring the protein interaction, for example the ALPHA technology, but while varying, for each repetition, the concentration of the compound to be tested. Varying the concentration of the compound to be tested has the advantage of specifying the inhibition capacities of the compound identified, by determining for example the dose-effect relationship of the compound. Measuring the interaction of the AIF and CHCHD4 proteins, by varying the concentration of the compound to be tested, makes it possible in particular to determine the median inhibitory concentration (IC50) of said compound. The IC50 gives an indication of the concentration of the compound required to inhibit by 50% the interaction between the AIF and CHCHD4 proteins and thus makes it possible to evaluate the efficacy of said compound with respect to inhibiting the interaction.

In one particular embodiment, the method comprises:

carrying out steps (a), (b) and (c) as described above, wherein the interaction of the AIF and CHCHD4 proteins is measured by means of an ALPHA assay; and repeating steps (a), (b) and (c) as described above, wherein the interaction of the AIF and CHCHD4 proteins is measured by means of an SPR assay.

In one particular embodiment, the method comprises, in this order:

carrying out steps (a), (b) and (c) as described above, wherein the interaction of the AIF and CHCHD4 proteins is measured by means of an ALPHA assay by a high-throughput screening experiment using a library of compounds to be tested;

selecting the compounds capable of inhibiting the interaction of the AIF and CHCHD4 proteins by at least 50%;

determining the dose-effect for each compound selected, which comprises repeating steps (a), (b) and (c) as described above while varying the concentration of the compound selected and by measuring the interaction of the AIF and CHCHD4 proteins by means of an ALPHA assay; and repeating steps (a), (b) and (c) as described above with the compounds selected, wherein the interaction of the AIF and CHCHD4 proteins is measured by means of an SPR assay.

In one particular embodiment, the method of the invention comprises carrying out steps (a), (b) and (c) as described above, wherein the compound is a compound capable of inhibiting the interaction between the AIF protein and the CHCHD4 protein. The use of a compound capable of inhibiting the interaction between the AIF protein and the CHCHD4 protein can thus serve as a positive control, making it possible to validate the experiment.

In one particular embodiment, said compound capable of inhibiting the interaction between the AIF protein and the CHCHD4 protein consists of the sequence of SEQ ID NO: 4, or consists of the sequence of SEQ ID NO: 4 or any functional variant having at least 708, 808, 90%, or at least 99%, identity with the sequence of SEQ ID NO: 4. The term "functional variant" is here understood to mean any variant of the sequence SEQ ID NO. 4 which variant is capable of inhibiting the interaction between the AIF protein and the CHCHD4 protein.

In one particular embodiment, said compound capable of inhibiting the interaction between the AIF protein and the CHCHD4 protein is selected from the group consisting of: disulfiram, bromocriptine or a salt thereof such as bromocriptine mesylate, thioridazine or a salt thereof such as thioridazine hydrochloride, Chicago sky blue 6B, mitoxantrone or a salt thereof such as mitoxantrone dihydrochloride, rifapentine, tetraethylenepentamine or a salt thereof such as tetraethylenepentamine penta-hydrochloride, nisoldipine, merbromine, triethylperazine or a salt thereof such as triethylperazine dimalate, and benidipine or a salt thereof as benidipine such hydrochloride.

In one particular embodiment, the method of the invention comprises a step of comparing the inhibition of the interaction of the AIF and CHCHD4 proteins obtained in the presence of the compound to be tested and the inhibition of the interaction obtained in the presence of the compound capable of inhibiting the interaction between the AIF protein and the CHCHD4 protein. In one particular embodiment, the compound is identified as potentially useful in the treatment of cancer if the inhibition obtained with the compound corresponds to at least 30%, 40%, 50%, 60%, 70%, 80% or at least 90% of the inhibition obtained with the positive control, namely with the N27 peptide. In particular, the compound is identified as potentially useful in the treatment of cancer if the inhibition obtained with the compound corresponds to at least 50% of the inhibition obtained with the positive control, namely with the N27 peptide.

Confirming the Anticancer Properties of the Compound

In one particular embodiment, the method of the invention also comprises a step of confirming, in a nonhuman animal or cell model of cancer, the anticancer properties of the compound identified as capable of inhibiting the interaction between the AIF and CHCHD4 proteins.

In one particular embodiment, the method of the invention comprises a step of administering the compound identified, in an animal model of cancer, then a step of analyzing the anticancer properties of said compound. Any animal model of cancer can be used, the animal preferably being a mammal. In particular, the animal may be a mouse, a rat, a pig, a rabbit, a chicken or a nonhuman primate.

In one particular embodiment, the method of the invention comprises a step of contacting the compound identified with a cell model of cancer, then a step of analyzing the cytotoxic properties of said compound. It may be a two-dimensional (2D) or three-dimensional (3D) cultured cell model. Any cell model of cancer can be used, such as a cancer cell line. For example, the compound identified may be brought into contact with the A549, MCF7 or HCT116 cancer cell lines.

2—Kit

Another aspect of the invention relates to a kit for identifying a compound potentially useful for the treatment of cancer, characterized in that it comprises:

an AIF protein;

a CHCHD4 protein; and means suitable for measuring the interaction between the AIF protein and the CHCHD4 protein.

In the context of the present invention, the AIF protein may be of any origin, preferably of animal origin, in particular a mammal, more preferentially of human origin. In one particular embodiment, the AIF protein corresponds to the human natural AIF protein, the NCBI sequence reference of which is "NP 004199.1", or any functional variant thereof. In particular, the AIF protein according to the invention may correspond to the natural human polypeptide of sequence SEQ ID NO: 1, or any functional variant, such as AIF2 which is a specific brain isoform. The expression "functional variant" which refers to the AIF protein denotes any polypeptide derived from the structure of the AIF protein and which retains the capacity of binding to the CHCHD4 protein, in particular to the CHCHD4 protein of SEQ ID NO: 2. The functional variants may be natural or synthetic variants, such as fragments, mutants or deletants. Preferably, the functional variant of the AIF protein corresponds to a polypeptide having a sequence identity of at least 50%, 60%, 70%, 80%, 90%, or at least 95%, with the AIF protein of sequence SEQ ID NO: 1.

In the context of the present invention, the CHCHD4 protein may be of any origin, preferably of animal origin, in particular a mammal, more preferentially of human origin. In one particular embodiment, the CHCHD4 protein corresponds to the human natural CHCHD4 protein, the NCBI sequence reference of which is "NP 001091972.1". In particular, the CHCHD4 protein according to the invention may correspond to the natural human polypeptide of sequence SEQ ID NO: 2 or any functional variant. The expression "functional variant" which refers to the CHCHD4 protein denotes any polypeptide derived from the structure of the CHCHD4 protein and which retains the capacity of binding to the AIF protein, in particular to the AIF protein of SEQ ID NO: 1. The functional variants may be natural or synthetic variants, such as fragments, mutants or deletants. Preferably, the functional variant of the CHCHD4 protein corresponds to a polypeptide having a sequence identity of at least 50%, 60%, 70%, 80%, 90%, or at least 95%, with the CHCHD4 protein of sequence SEQ ID NO: 2.

In one particular embodiment, the functional variant of the AIF protein is deleted or truncated compared to the AIF of protein ID NO: 1. SEQ In particular, the functional variant of the AIF protein may correspond to a polypeptide from which the transmembrane part of the deleted. In one particular AIF protein has been embodiment, the functional variant of the AIF protein corresponds to a polypeptide of sequence SEQ ID NO: 3.

The AIF and CHCHD4 proteins can be modified, provided that this does not prevent the interaction between the two proteins. For example, for the needs of the experiment to measure their interaction, the AIF and/or CHCHD4 proteins can be fused to a fragment serving as a tag. Any conventional tag can be used, provided that it does not prevent the interaction between the two proteins. In particular, the AIF and/or CHCHD4 proteins can be fused to a Histidine tag corresponding to a motif consisting of several histidine residues, or to a GST tag corresponding to the glutathione-S-transferase protein.

The expression "means suitable for measuring the interaction between the AIF protein and the CHCHD4 protein" is intended to mean any means, for example any reagent, compound, material, support or composition, required for carrying out the technique of measuring the interaction between said proteins.

The means suitable for measuring the interaction between the AIF protein and the CHCHD4 protein may be means suitable for any technique which makes it possible to measure or quantify the interaction between two proteins. For example, the kit may comprise means suitable for an luminescent proximity homogeneous assay amplified (ALPHA), a surface plasmon resonance (SPR) assay, a thermal shift assay (TSA) method, an immunoprecipitation method, an isothermal titration calorimetry (ITC) assay, a fluorescence resonance energy transfer (FRET) assay, a fluorescence polarization assay and/or an ELISA assay.

Preferably, the means suitable for measuring the interaction between the AIF protein and the CHCHD4 protein are applicable to high-throughput screening.

In one particular embodiment, the kit comprises means suitable for an ALPHA assay and/or for an SPR assay.

In one preferred embodiment, the kit comprises means suitable for measuring the interaction between the AIF and CHCHD4 protein by means of an ALPHA assay. In particular, the kit can comprise:

- an AIF protein;
- a CHCHD4 protein;
- donor beads capable of emitting reactive oxygen species, such as singlet oxygens, when they are excited at a given wavelength, preferably of approximately 680 nm; and
- acceptor beads capable of emitting a light signal, preferably between 520 nm and 620 nm, following the reaction with reactive oxygen species, such as singlet oxygens;
- the donor and acceptor beads also being capable of conjugating with one or other of the AIF or CHCHD4 proteins.

In one particular embodiment, the donor beads and the acceptor beads are covered with molecules or functional groups which allow them to be conjugated with one or other of the AIF or CHCHD4 proteins. In particular, the donor and acceptor beads can be covered with a layer of nickel, of glutathione, of streptavidin, of protein A, G or L or of antibodies. In one particular embodiment, the donor beads are covered with nickel and the acceptor beads are covered with glutathione.

In one particular embodiment, the donor beads included in the kit are preconjugated to one or the other of the AIF or CHCHD4 proteins. In one particular embodiment, the acceptor beads included in the kit are preconjugated to one or the other of the AIF or CHCHD4 proteins.

In one particular embodiment, the donor and acceptor beads are beads from the Alphascreen® or Alphalisa® commercial assay (PerkinElmer).

Optionally, the kit as described above may comprise a buffer suitable for the experiment to measure the interaction between the AIF protein and the CHCHD4 protein. The term "buffer" is intended to mean any solution in which the AIF and CHCHD4 proteins, the compound to be tested and, optionally, the means suitable for measuring the interaction of the proteins are brought into contact. The buffer is chosen so as not to inhibit the interaction between the AIF and CHCHD4 proteins. Thus, the buffer may also serve as a negative control during the implementation of the method of the invention.

In one particular embodiment, the kit comprises a buffer suitable for an ALPHA assay.

In one particular embodiment, the buffer comprises phosphate buffered saline (PBS) and bovine serum albumin (BSA). In one particular embodiment, the buffer comprises PBS and 0.1% of BSA.

Optionally, the kit as described above can comprise a compound capable of inhibiting the interaction between the AIF protein and the CHCHD4 protein. The compound capable of inhibiting the interaction between the AIF protein and the CHCHD4 protein can thus serve as a positive control, making it possible to validate the experiment to measure the interaction between the AIF and CHCHD4 proteins, during the implementation of the method of the invention.

In one particular embodiment, said compound capable of inhibiting the interaction between the AIF protein and the CHCHD4 protein consists of the sequence of SEQ ID NO: 4 or any functional variant having at least 708, 80%, 90%, or at least 99%, identity with the sequence of SEQ ID NO: 4. By "functional variant" is meant any variant of the sequence SEQ ID NO: 4, which variant is capable of inhibiting the interaction between the AIF protein and the CHCHD4 protein.

In one particular embodiment, said compound capable of inhibiting the interaction between the AIF protein and the CHCHD4 protein is selected from the group consisting of: disulfiram, bromocriptine or a salt thereof such as bromocriptine mesylate, thioridazine or a salt thereof such as thioridazine hydrochloride, Chicago sky blue 6B, mitoxantrone or a salt thereof such as mitoxantrone dihydrochloride, rifapentine, tetraethylenepentamine or a salt thereof such as tetraethylenepentamine penta-hydrochloride, nisoldipine, merbromine, thiethylperazine or a salt thereof such as thiethylperazine dimalate, and benidipine or a salt thereof such as benidipine hydrochloride.

The kit as described above may also comprise any support suitable for the experiment to measure the interaction between the AIF protein and the CHCHD4 protein. For example, the support can be chosen from a plate, a tube, a flask, a membrane, etc. In particular, the support may be a multiwell plate, thereby making it possible to carry out numerous and varied assays in parallel. Among the typical supports are microtitration plates and more particularly 96-well or 384-well (or more) plates which are easy to handle.

One aspect of the invention also relates to the use of the kit as described above, in a method for identifying a compound potentially useful for the treatment of cancer.

4—Composition

Another aspect of the invention relates to a pharmaceutical composition comprising a compound identified by the method as described above, in combination with a pharmaceutically acceptable carrier.

Thus, one aspect of the invention relates to a pharmaceutical composition comprising a compound capable of inhibiting the interaction between the AIF and CHCHD4 proteins, in combination with a pharmaceutically acceptable carrier.

The term "pharmaceutically acceptable carrier" should be understood to mean any substance other than the active ingredient in a medicament. The addition thereof is intended to confer physicochemical and/or biochemical characteristics for facilitating oral, sublingual, respiratory, rectal, nasal, intestinal, parenteral administration, or administration by intravenous, intraperitoneal, intramuscular, subcutaneous injection, or other particular consistency or gustative characteristics, on the final product, while preferably avoiding covalent chemical interactions with the active ingredients.

The pharmaceutical compositions of the invention may be in the form of simple or sugar-coated tablets, of sublingual tablets, of capsules, gel of orally disintegrating tablets, of capsules, of lozenges, of injectable preparations, of aerosols, of nasal drops, of suppositories, or of creams, ointments or dermal gels.

5—Uses

Another aspect of the invention relates to a compound identified by the method as described above, for use thereof as a medicament. Thus, one aspect of the invention relates to a compound capable of inhibiting the interaction between the AIF and CHCHD4 proteins, for use thereof as a medicament.

In particular, one aspect of the invention relates to a compound identified by the method as described above, for use thereof in a method for treating cancer. Thus, one aspect of the invention relates to a compound capable of inhibiting the interaction between the AIF and CHCHD4 proteins, for use thereof in a method for treating cancer.

In one particular embodiment, the compound capable of inhibiting the interaction between the AIF and CHCHD4 proteins is selected from the group consisting of: Chicago sky 6B, blue rifapentine, nisoldipine, merbromine, thiethylperazine or a salt thereof such as thiethylperazine dimalate, and benidipine or a salt thereof such as benidipine hydrochloride.

It is herein described a method for treating a cancer in a subject, comprising the administration to said subject of a compound capable of inhibiting the interaction between the AIF and CHCHD4 proteins or of the pharmaceutical composition comprising said compound.

The treatment method may comprise the administration of the compound capable of inhibiting the interaction between the AIF and CHCHD4 proteins or of the pharmaceutical composition comprising said compound, alone or in combination with any anticancer treatment such as radiotherapy, chemotherapy and immunotherapy. In particular, the treatment method may comprise the administration of said compound capable of inhibiting the interaction between the AIF and CHCHD4 proteins, in combination with the administration of a chemotherapy agent. The administration of the compound capable of inhibiting the interaction between the AIF and CHCHD4 proteins can be carried out prior to, simultaneously with, or subsequent to the administration of the chemotherapy agent. The term "chemotherapy agent" is intended to mean a chemical product which can be used to destroy a cancer cell, or to slow down, stop or reverse the growth of a cancer cell.

In the context of the invention, the term "subject" or "patient" denotes an animal, preferably a mammal, in particular a human being, regardless of the age or sex thereof, suffering from cancer. The term includes domestic animals and also laboratory animals such as nonhuman primates, felines, canines, members of the equine family, members of the porcine family, bovines, goats, sheep, rabbits, rats and mice. Preferably, the patient to be treated is a human being.

As used here, the term "cancer" denotes any type of malignant tumor. The malignant tumor may correspond to a primary tumor or to a secondary tumor (that is to say a metastasis). In addition, the tumor may correspond to a solid malignant tumor, which comprises for example carcinomas, adenocarcinomas, sarcomas, melanomas, mesotheliomas, and blastomas or to a blood cell cancer such as leukemias, lymphomas and myelomas. The cancer may for example correspond to a skin, lung, bladder, kidney cancer, to a digestive cancer (colon, pancreas, liver), ovarian cancer, brain cancer, cancer of the face and neck, etc.

The term "treatment" comprises a curative and/or preventive treatment. A curative treatment refers to the reduction, improvement, stabilization and/or elimination of a symptom of the disease, or else to the inhibition of the progression of a symptom of the disease. A preventive treatment refers to any one of the following effects: preventing or delaying the appearance of a given disorder, reducing the development, the risk of development, the incidence or the seriousness of a disorder, increasing the delay of appearance of the symptoms and/or the survival of the patient.

Another aspect of the invention relates to the use in academic research of a compound identified by the method as described above, for use thereof as a compound for disrupting mitochondrial import and/or cell metabolism. In one particular embodiment, said compound capable of inhibiting the interaction between the AIF protein and the CHCHD4 protein is selected from the group consisting of: disulfiram, bromocriptine or a salt thereof such as bromocriptine mesylate, thioridazine or a salt thereof such as thioridazine hydrochloride, Chicago sky blue 6B, mitoxantrone or a thereof such salt as mitoxantrone dihydrochloride, rifapentine, tetraethylenepentamine or a salt thereof such as tetraethylenepentamine penta-hydrochloride, nisoldipine, merbromine, thiethylperazine or a salt thereof such as thiethylperazine dimalate, and benidipine or a salt thereof such as benidipine hydrochloride.

Examples

Materials and Methods

Abbreviations

AIF apoptosis-inducing factor
BSA bovine serum albumin
CHCHD4 Coiled-Coil-Helix-Coiled-Coil-Helix (CHCH) Domain containing 4
IC50 median inhibitory concentration
CV coefficient of variation
DMSO dimethyl sulfoxide
GST Glutathione-S-transferase
HIS histidine
HTS High Throughput Screening
MEF Mouse embryonic fibroblast
PBS phosphate buffered saline
RT room temperature
RU resonance unit S/B signal over background ratio
SD standard deviation
SPR surface plasmon resonance
TH threshold Protein Expression and Purification The AIF103-613 protein (AIF protein fragment 103-613) and CHCHD4 protein were produced in BL21+DE3 bacteria (RIPL), via an induction for 3 hours with 0.5 mM IPTG at 37° C. The bacteria were transformed according to the recommendations of the supplier (Agilent). The proteins were then purified. The total protein concentration was determined using a Bradford assay kit. The purity of the expression was also evaluated on a polyacrylamide gel in the presence of SDS.

Assay for the Interaction of the AIF and CHCHD4 Proteins and Identification of Compounds Modulating this Interaction by Means of an Alpha Assay A method enabling the identification of compounds capable of inhibiting the interaction between the AIF and CHCHD4 proteins and suitable for high-throughput screening was developed. This method comprises the use:

of the AIF103-613 and CHCHD4 proteins previously produced;

of an AlphaScreen® kit (PerkinElmer) comprising donor beads and acceptor beads capable of conjugating to the AIF and CHCHD4 proteins;

of a positive control: the N27 peptide (corresponding to the 27 amino acids of the N-ter end of the CHCHD4 protein, as described in Hangen et al., 2015);

of a negative control: 0.1% bovine serum albumin (BSA) solution in phosphate buffered saline (PBS);

of a library of compounds to be tested: the Prestwick chemical compound library (Prestwick Chemical Library®).

The ALPHA assay was first of all carried out at high throughput, using 384-well white microplates (Greiner, reference 781075), using 25 μl of total volume per well. The proteins, the positive control and the beads were diluted in a 0.1% BSA/PBS solution. All the distributions were carried out with an electronic multipipet, then the plates were centrifuged (200 g, 1 min). The plates were hermetically closed and incubated in the dark in a room at 23° C.

A library of 1280 small molecules, supplied by Prestwick Chemicals (Prestwick Chemical Library®) was screened. This library comprises compounds with various chemical and pharmacological properties, which are already approved by the health authorities, such as the FDA (Food and Drug Administration) or the EMEA (European Medicines Evaluation Agency). Each compound of the library is diluted in a 0.1% DMSO solution and used at a concentration of 10 μM. First of all, 5 μl of compound at 10 μM, of N27 at 3 μM (positive control) or of 0.1% BSA/PBS (negative control) were added to the wells. Secondly, 5 μl of AIF103-613 proteins were incubated with the compounds for 20 min before the addition of 5 μl of CHCHD4 for 2 h. Thirdly, 10 μl of a mixture of donor beads and acceptor beads at 5 μg/ml were incubated for 3 h. The analysis of the results was carried out by means of an EnSpire® multimode plate reader (PerkinElmer). The interaction of the AIF and CHCHD4 proteins is revealed by detection of a light signal by the plate reader.

Analysis of the Data of the ALPHA Assay

For each experiment to measure the interaction of the AIF and CHCHD4 proteins, 3 measurements validating the quality of the experiment were carried out: the coefficient of variation of the controls (CV), the signal/background noise (S/B) ratio and the Z' factor as described below.

For each 384-well plate, 16 wells correspond to the positive control and 16 wells correspond to the negative control. The positive control corresponds to the measurement of the interaction of the AIF103-613 and CHCHD4 proteins in the presence of the N27 peptide (equivalent to the minimal signal). The negative control corresponds to the measurement of the interaction of the AIF103-613 and CHCHD4 proteins in the presence of the buffer (0.1% BSA/PBS) (equivalent to the maximum signal).

CV is defined as the ratio of the standard deviation (SD) divided by the mean of each control:

$$\frac{SD\ (\text{signal of the control})}{\text{mean (signal of the control)}}\ 100$$

S/B is the ratio corresponding to the mean of the negative controls, divided by the mean of the positive controls:

$$\frac{\text{signal}}{\text{background noise}} = \frac{\text{mean (signal of the negative control)}}{\text{mean (signal of the positive control)}}$$

The Z' factor evaluates the amplitude of the signal of an assay, by measuring the difference between the positive and negative controls, and taking into account the standard deviations (SD):

$$1 - \frac{3 \times (SD\ (\text{signal of the positive control}) + SD\ (\text{signal of the negative control}))}{[\text{mean (signal of the positive control)} - \text{mean (signal of the positive control)}]}$$

Each series of measurements is validated if CV<15%, S/B>10 and the Z' factor>0.5 [Goktug et al., Drug Discovery, 2013 doi10.5772/52508].

Following the high-throughput screening, the compounds are selected if the signal obtained in the presence of the compound is less than the following threshold TH:

TH=mean (signal of the negative control)−5×SD (signal of the negative control)

For each compound previously selected, the ALPHA assay is repeated manually using another batch of powder of the compounds.

Each compound is tested at 10 μM and 30 μM due to the Hook effect particular to the ALPHAscreen technology and in order to select the compounds giving a signal located in the ascending part of the Hook bell and therefore active at low dose in a drug development perspective.

The compound is selected if:

the signal obtained in the presence of the compound is less than the threshold TH as described above; and the signal obtained at 30 μM is less than the signal obtained at 10 μM.

In addition, for each compound thus selected, the dose-effect relationship of the compound is determined. This makes it possible to determine the median inhibitory concentration (IC50) of said compound.

Validation of the Compounds Inhibiting the Interaction of the AIF and CHCHD4 Proteins by Means of an SPR Assay Some of the compounds identified by means of the Alpha assay as described above were tested by surface plasmon resonance (Biacore™ T100, GE Healthcare Life Sciences). The CHCHD4 protein was immobilized covalently on a dextran matrix comprising COOH functional carboxyl groups (Series S CM5® sensor chip, GE Healthcare Life Sciences, 29149603). In order to carry out the screening, the compounds (at 10 UM) were preincubated for 20 min with the AIF protein, at ambient temperature in a DPBS buffer at pH 7.4 (Sigma, D8577). Next, the mixture of the compound and the AIF protein was injected for 3 min at 30 µl per minute at 25° C. A negative control was performed by injecting the AIF protein alone at 1 µM (diluted in 0.1% DMSO/PBS). A positive control was performed by injecting a mixture of N27 peptide (at 3 µM) and AIF protein.

A compound is validated if it is capable of significantly decreasing the interaction between AIF103-613 and CHCHD4, that is to say if the inhibition obtained with the compound corresponds to at least 50% of the inhibition obtained with the positive control, namely with the N27 peptide. The sensorgrams were analyzed using the BIAevaluation software (Version 2.0.4).

Effect of the Hits on Cellular Energy Metabolism and their Cytoxicity

The effect of the compounds on the metabolism of a non-small-cell lung cancer cell line (A549) was tested using the Seahorse technology (XFe96, Agilent) and the cell death was evaluated by measuring the release of lactate dehydrogenase (LDH, Promega). The cells seeded into 96-well microplates (20 000 cells/well) were treated with the compounds as a dose response (0.03; 0.1; 0.3; 1; 3; 10 µM) for 3 h in serum-free DMEM medium and then mitochondrial respiration (OXPHOS) and glycolysis were measured in real time. At the end of the experiment, the culture supernatant was removed in order to analyze the cell death, and the number of cells was determined by counting, after labelling the cells with DAPI, using a fluorescence microscope (Zeiss). The number of cells per well at the end of the experiment was then used to normalize the results obtained by Seahorse.

Results

Development of the Protocol and Optimization for the High-Throughput Screening

The concentrations of AIF103-613 and CHCHD4 proteins required for obtaining an optimal signal in Alphascreen® were evaluated. FIG. 1 shows that the optimal signal obtained with AIF103-613 and CHCHD4 is dose dependent. The batches of proteins, peptide and reagents were then verified in a preliminary experiment and obtain a Z'>0.5 (not shown).

Summary of the Statistics Obtained by High-Throughput Screening in 384-Well Plates The Prestwick library (1280 molecules) was then screened using four 384-well plates (Plate #1 to #4).

Before the screening itself, all the reagents (proteins, beads, buffers) and materials (plates, tips, pipetter) are subjected to a quality control called "prescreening validation assay" and a certain number of criteria are analyzed. As indicated above, each series of measurements is validated if CV<15%, S/B>10 and the Z' factor>0.5.

The statistical data obtained by high-throughput screening in 384-well plates are detailed in Table 1 below:

TABLE 1

| Analysis criteria | | Prescreening validation assays | Screening Plate #1 | Plate #2 | Plate #3 | Plate #4 |
|---|---|---|---|---|---|---|
| Number of positive and negative control wells | | 48 | 16 | 16 | 16 | 16 |
| Negative controls | Mean | 26354 | 22249 | 27593 | 30459 | 19650 |
| | SD | 2504 | 1303 | 1436 | 2170 | 712 |
| | CV (%) | 10 | 6 | 5 | 7 | 4 |
| Positive controls | Mean | 2123 | 1776 | 2242 | 2526 | 1833 |
| | SD | 290 | 146 | 120 | 289 | 131 |
| | CV (%) | 14 | 8 | 5 | 11 | 7 |
| S/B | | 12.4 | 13 | 12 | 12 | 11 |
| Z' factor | | 0.65 | 0.79 | 0.82 | 0.74 | 0.86 |

Figure 2:
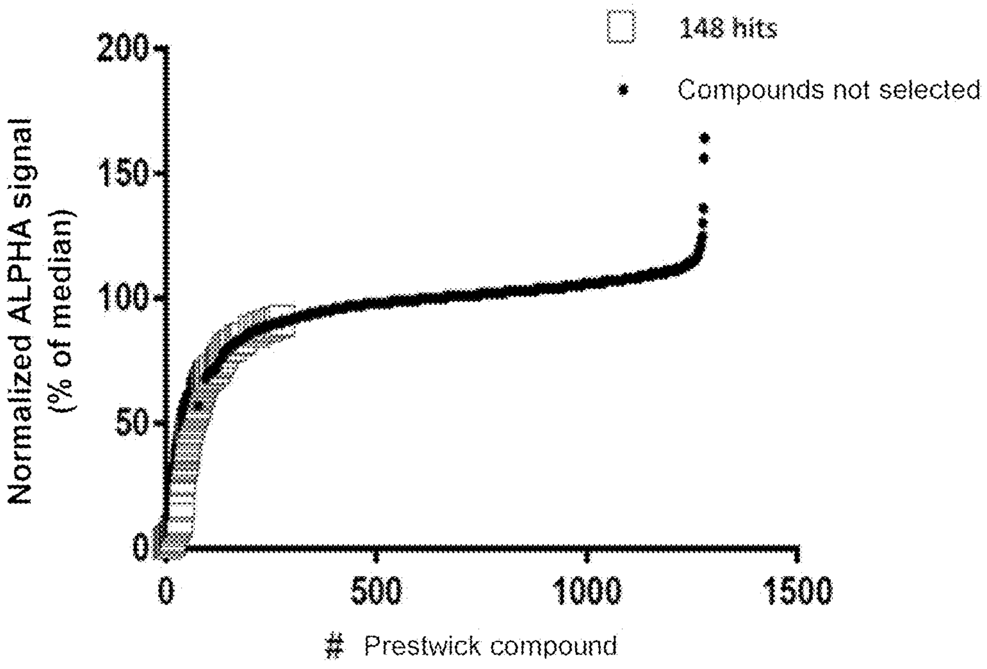
FIG. 2: inhibition of the AIF103-613/CHCHD4 interaction. The Prestwick library consisting of 1280 compounds was screened, by means of an Alphascreen assay at a concentration of 10 μM. The compounds selected are identified by white squares, the black dots correspond to the compounds not selected. The compound is selected if the raw signal obtained in the presence of the compound is lower than a threshold value TH (TH=mean (signal of the negative control)−5×SD (signal of the negative control)). The Y axis corresponds to the normalized signal, namely the signal calculated as percentage of the mean.

Identification of Compounds Inhibiting the Interaction Between the AIF and CHCHD4 Proteins 1) Identification of the Compounds by Means of an ALPHA Assay The Prestwick compound library, comprising 1280 molecules, was screened using four 384-well plates, as described above. The compounds were selected on the basis of the signal obtained in Alphascreen® in the presence of the compound at a concentration of 10 µM. In particular, the compound is selected if the signal obtained at 10 µM is less than a threshold value TH (TH=mean (signal of the negative control)−5×SD (signal of the negative control)). Out of the 1280 compounds analyzed, 148 were selected, i.e. 12% of the compound library (cf. FIG. 2).

The 148 compounds selected were again tested by means of an ALPHA assay carried out manually, as described above. Out of the 148 compounds tested, 11 compounds were finally selected. For the 11 compounds selected:

- the signal obtained at 10 µM is less than the threshold value TH; and
- the signal obtained at 30 µM is less than the signal obtained at 10 µM.

Table 2 below lists the 11 compounds selected by ALPHA screen. The CAS numbers and the chemical structures of each compound are reported in Table 2 below.

TABLE 2a
| | Compound name | CAS No. | Chemical structure |
|---|---|---|---|
| 1 | Disulfiram | 97-77-8 | 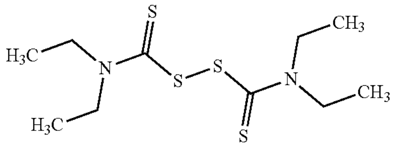 [SMILES: CCN(CC)C(=S)SSC(=S)N(CC)CC] |
| 2 | Bromocriptine mesylate | 22260-51-1 | 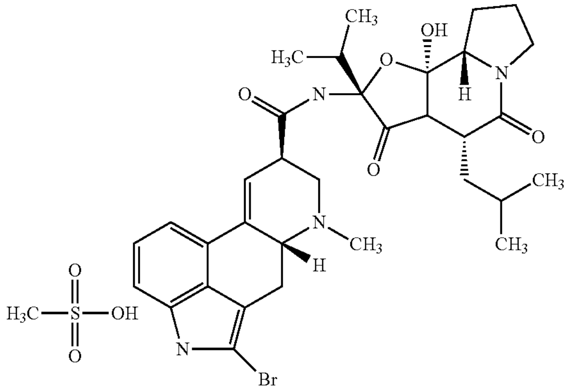 |
| 3 | Thioridazine hydrochloride | 130-61-0 | 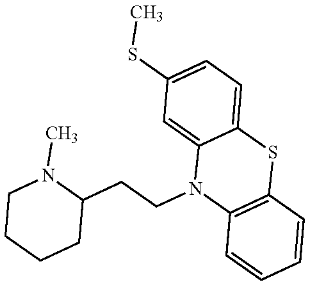 [SMILES: CSc1ccc2c(c1)N(CCC1CCCCN1C)c1ccccc1S2] |
| 4 | Chicago sky blue 6B | 2610-05-1 | 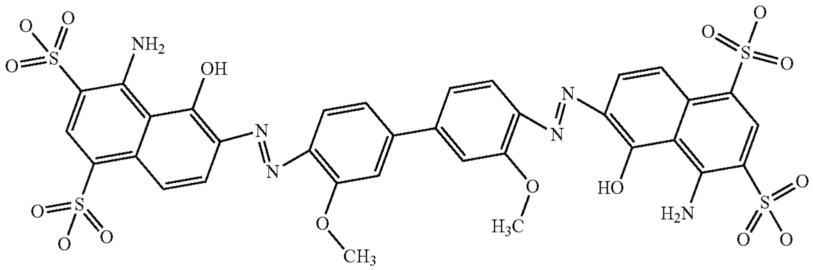 [SMILES: COc1cc(-c2ccc(/N=N/c3ccc4c(S(=O)(=O)O)cc(S(=O)(=O)O)c(N)c4c3O)c(OC)c2)ccc1/N=N/c1ccc2c(S(=O)(=O)O)cc(S(=O)(=O)O)c(N)c2c1O] |
TABLE 2b
| | | | |
|---|---|---|---|
| 5 | Mitoxantrone dihydrochloride | 70476-82-3 | 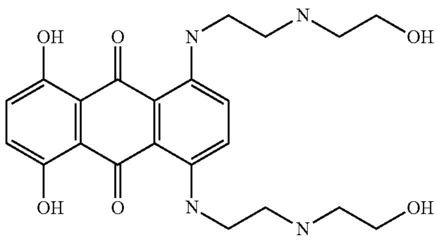 [SMILES: O=C1c2c(O)ccc(O)c2C(=O)c2c(NCCNCCO)ccc(NCCNCCO)c21] |

TABLE 2b-continued
| | | | |
|---|---|---|---|
| 6 | Rifapentine | 61379-65-5 | 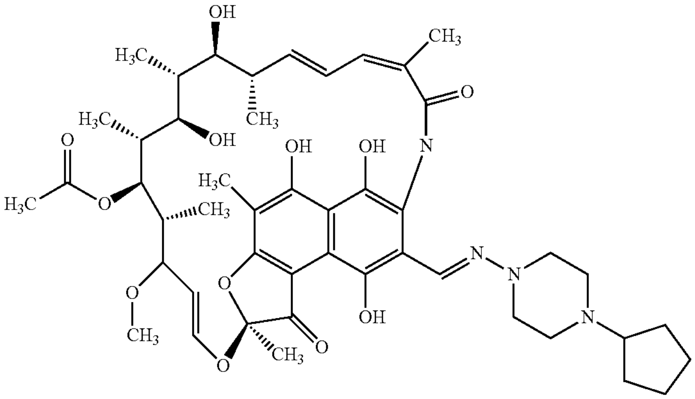 [SMILES: COC1/C=C/O[C@@]2(C)Oc3c(C)c(O)c4c(O)c(c(/C=N/N5CCN(C6CCCC6)CC5)c(O)c4c3C2=O)NC(=O)/C(C)=C\C=C\[C@H](C)[C@H](O)[C@@H](C)[C@@H](O)[C@@H](C)[C@H](OC(C)=O)[C@@H]1C] |
| 7 | Tetraethylenepentamine pentahydrochloride | 4961-43-5 | 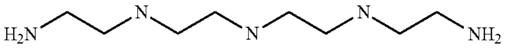 |
| 8 | Nisoldipine | 63675-72-9 | 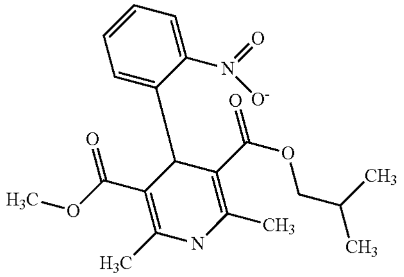 |
TABLE 2c
| | | | |
|---|---|---|---|
| 9 | Merbromine | 129-16-8 | 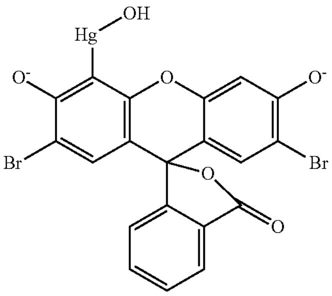 |
| 10 | Thiethylperazine dimalate | 52239-63-1 | 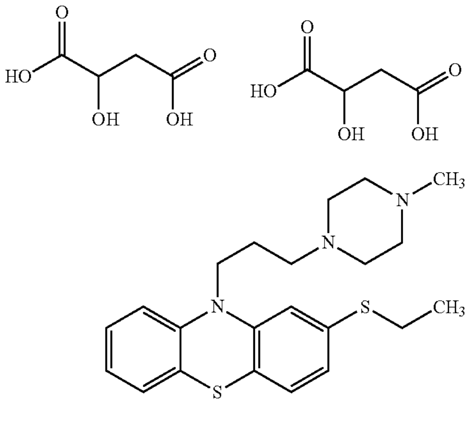 |

TABLE 2c-continued

| | | | |
|---|---|---|---|
| 11 | Benidipine hydrochloride | 91599-74-5 | 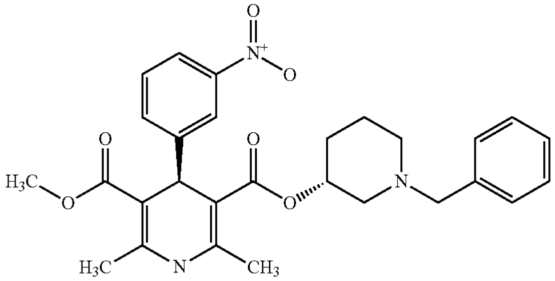 |

The anticancer properties of some of these compounds have already been demonstrated, thus validating the screening method of the present invention. For example, the anticancer properties of thioridazine are described in the article by Shen et al., 2017. In addition, mitoxantrone is sold as an anticancer agent (under the name NovantroneR), in particular in the treatment of metastatic breast cancer, of non-Hodgkin's lymphoma or else of acute myeloid leukemia (AML).

Table 3 below lists the IC50 values of the 11 compounds identified, said values having been obtained manually using the Alphascreen assay:

TABLE 3

| Compound | IC50 AIF/CHCHD4 |
|---|---|
| Disulfiram | 415 nM |
| Bromocriptine mesylate | 4.57 μM |
| Thioridazine hydrochloride | 24 μM |
| Chicago sky blue 6B | 1.44 μM |
| Mitoxantrone dihydrochloride | 1.27 μM |
| Rifapentine | 4.8 μM |
| Tetraethylenepentamine pentahydrochloride | 9 μM |
| Nisoldipine | 12 μM |
| Merbromine | 169 nM |
| Thiethylperazine dimalate | 10.6 μM |
| Benidipine hydrochloride | 8 μM |

Figure 3:
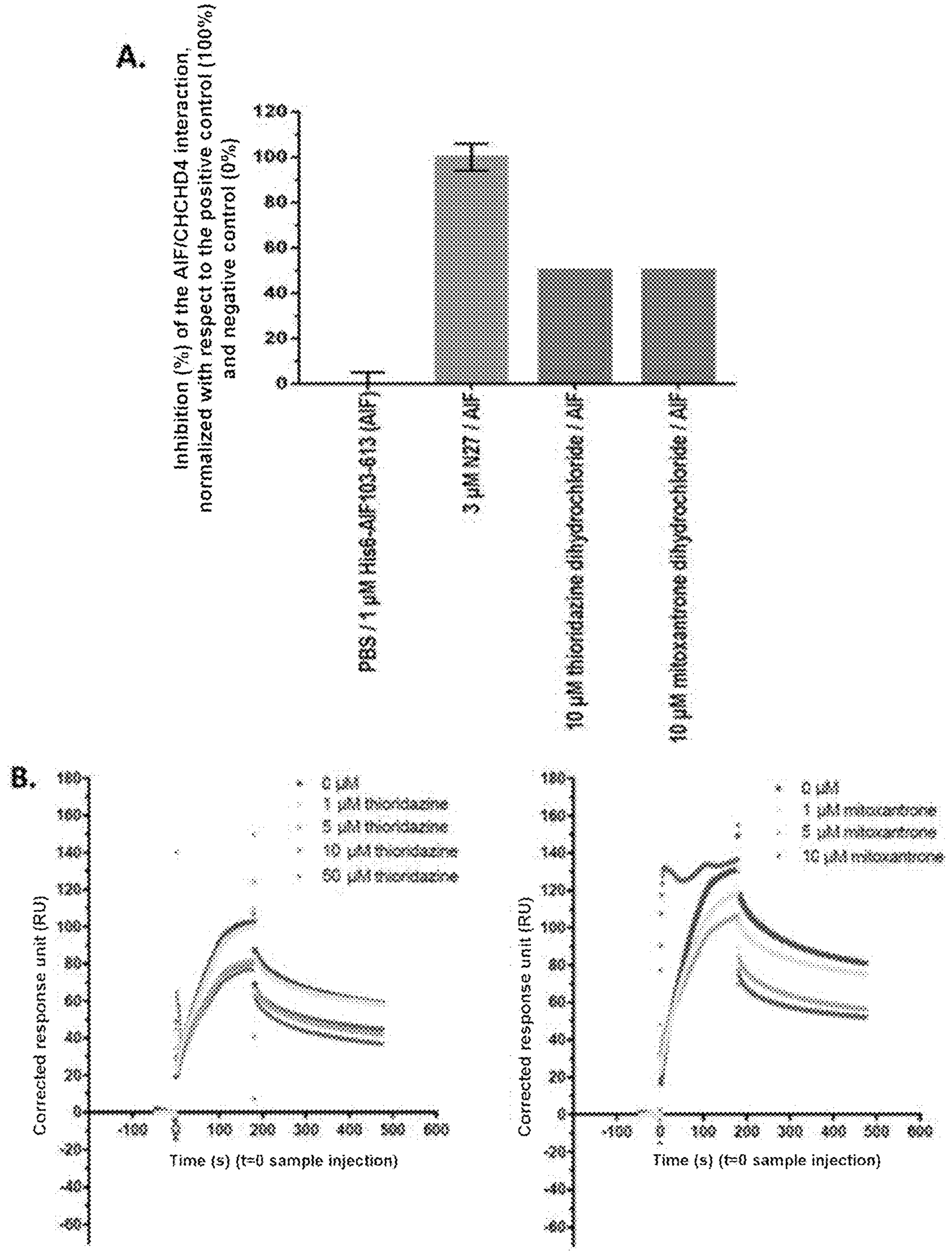
FIG. 3: SPR analysis of the compounds identified by Alphascreen. (A) SPR validation of thioridazine and of mitoxantrone, by means of the Alphascreen assay, as inhibitors of the AIF103-613/CHCHD4 interaction. The compounds at 10 μM were incubated for 20 min with AIF in DPBS at pH 7.4 at ambient temperature. Then, the mixture was then injected for 3 minutes at a rate of 30 μl per minute onto the CHCHD4 protein. The N27 peptide at 3 UM was used as a negative control. (B) Surface plasmon resonance (SPR) sensorgrams, making it possible to follow the binding of AIF103-613 to CHCHD4 in the presence of thioridazine hydrochloride or of mitoxantrone dihydrochloride. The thioridazine hydrochloride and the mitoxantrone dihydrochloride were tested at increasing concentrations ranging from 0.5 μM to 50 μM.

2) Confirmation of the Inhibition of the Interaction of the AIF and CHCHD4 Proteins by Means of an SPR Assay The inhibition of the interaction of the AIF and CHCHD4 proteins by thioridazine and mitoxantrone was analyzed by means of a surface plasmon resonance assay (cf. FIG. 3). A compound is considered to inhibit the interaction of the AIF and CHCHD4 proteins if the inhibition obtained with the compound corresponds to at least 50% of the inhibition obtained with the positive control, namely with the N27 peptide.

The surface plasmon resonance assay confirmed that thioridazine and mitoxantrone are capable of inhibiting the interaction between the AIF and CHCHD4 proteins.

3) Confirmation of the Cytotoxic Properties of the Compounds

Table 4 below demonstrates the cytotoxic properties of certain compounds toward non-small-cell lung cancer cells (A549 human cell line). The compound concentration indicated in the "toxicity" column represents the lowest dose tested for which a toxicity greater than 20% was measured.

TABLE 4

| Compound | Cellular toxicity (μM) |
|---|---|
| Disulfiram | 3 |
| Bromocriptine mesylate | 3 |
| Thioridazine hydrochloride | 1 |
| Mitoxantrone dihydrochloride | 3 |
| Rifapentine | 10 |
| Tetraethylenepentamine pentahydrochloride | 10 |
| Thiethylperazine dimalate | 10 |
| Benidipine hydrochloride | 10 |

The table shows that a 3 h treatment with the compounds induces A549 cell cytotoxicity in the concentration range tested (cf. method described above). In addition, the experiments demonstrated that the compounds act on the energy metabolism whether by modulation of glycolysis or by modulation of mitochondrial activity.

Thus, these results confirm the anticancer properties of the compounds identified by the screening method.

REFERENCES

Hangen, E., et al., Interaction between AIF and CHCHD4 regulates respiratory chain biogenesis. Molecular cell, 2015. 58 (6): pp. 1001-1014.

Shen, J., et al., Thioridazine has potent antitumor effects on lung cancer stem-like cells. Oncology letters, 2017. 13 (3): pp. 1563-1568.

The invention claimed is:

1. A method for identifying a compound potentially useful for the treatment of cancer comprising assessing the capacity of a compound to inhibit the interaction between apoptosis inducing factor (AIF) protein and coiled-coil-helix-coiled-coil-helix containing 4 (CHCHD4) protein, said compound being identified as potentially useful for the treatment of cancer if it inhibits said interaction, said method comprising:

(a) contacting the AIF protein and the CHCHD4 protein in the presence and in the absence of said compound;

(b) measuring the interaction between the AIF protein and the CHCHD4 protein, in the presence and in the absence of said compound;

(c) identifying the compound as potentially useful for the treatment of cancer if the measurement of said interaction is lower in the presence of said compound than in the absence of said compound; and (d) confirming, in a nonhuman animal or cell model of cancer, the anticancer properties of the compound identified in step (c).

2. The method according to claim 1, wherein said compound is identified as potentially useful for the treatment of cancer if it inhibits the interaction between the AIF protein and the CHCHD4 protein by at least 50%.

3. The method according to claim 1, wherein the measurement of the interaction between the AIF protein and the CHCHD4 protein is carried out by means of an amplified luminescent proximity homogeneous assay (ALPHA), a surface plasmon resonance (SPR) assay, a thermal shift assay (TSA) method, an immunoprecipitation method, an isothermal titration calorimetry (ITC) assay, a fluorescence resonance energy transfer (FRET) assay, a fluorescence polarization assay or an ELISA assay.

4. The method according to claim 1, wherein the compound is a chemical compound.

5. The method according to claim 1, said method comprising:

(i) determining the capacity of said compound to inhibit the interaction between the AIF protein and the CHCHD4 protein, by means of an amplified luminescent proximity homogeneous assay (ALPHA);

(ii) determining the capacity of said compound to inhibit the interaction between the AIF protein and the CHCHD4 protein, by means of a surface plasmon resonance (SPR) assay; and (iii) confirming, in a nonhuman animal or cell model of cancer, the anticancer properties of the compound identified.

* * * * *

SEQUENCE LISTING

```
<160> NUMBER OF SEQ ID NOS: 4

<210> SEQ ID NO 1
<211> LENGTH: 613
<212> TYPE: PRT
<213> ORGANISM: Homo sapiens
```

<400> SEQUENCE: 1

```
Met Phe Arg Cys Gly Gly Leu Ala Ala Gly Ala Leu Lys Gln Lys Leu
1               5                   10                  15

Val Pro Leu Val Arg Thr Val Cys Val Arg Ser Pro Arg Gln Arg Asn
            20                  25                  30

Arg Leu Pro Gly Asn Leu Phe Gln Arg Trp His Val Pro Leu Glu Leu
        35                  40                  45

Gln Met Thr Arg Gln Met Ala Ser Ser Gly Ala Ser Gly Gly Lys Ile
    50                  55                  60

Asp Asn Ser Val Leu Val Leu Ile Val Gly Leu Ser Thr Val Gly Ala
65                  70                  75                  80

Gly Ala Tyr Ala Tyr Lys Thr Met Lys Glu Asp Glu Lys Arg Tyr Asn
                85                  90                  95

Glu Arg Ile Ser Gly Leu Gly Leu Thr Pro Glu Gln Lys Gln Lys Lys
            100                 105                 110

Ala Ala Leu Ser Ala Ser Glu Gly Glu Glu Val Pro Gln Asp Lys Ala
        115                 120                 125

Pro Ser His Val Pro Phe Leu Leu Ile Gly Gly Gly Thr Ala Ala Phe
    130                 135                 140

Ala Ala Ala Arg Ser Ile Arg Ala Arg Asp Pro Gly Ala Arg Val Leu
145                 150                 155                 160

Ile Val Ser Glu Asp Pro Glu Leu Pro Tyr Met Arg Pro Pro Leu Ser
                165                 170                 175

Lys Glu Leu Trp Phe Ser Asp Asp Pro Asn Val Thr Lys Thr Leu Arg
            180                 185                 190

Phe Lys Gln Trp Asn Gly Lys Glu Arg Ser Ile Tyr Phe Gln Pro Pro
        195                 200                 205

Ser Phe Tyr Val Ser Ala Gln Asp Leu Pro His Ile Glu Asn Gly Gly
    210                 215                 220

Val Ala Val Leu Thr Gly Lys Lys Val Val Gln Leu Asp Val Arg Asp
225                 230                 235                 240

Asn Met Val Lys Leu Asn Asp Gly Ser Gln Ile Thr Tyr Glu Lys Cys
                245                 250                 255

Leu Ile Ala Thr Gly Gly Thr Pro Arg Ser Leu Ser Ala Ile Asp Arg
            260                 265                 270

Ala Gly Ala Glu Val Lys Ser Arg Thr Thr Leu Phe Arg Lys Ile Gly
        275                 280                 285

Asp Phe Arg Ser Leu Glu Lys Ile Ser Arg Glu Val Lys Ser Ile Thr
    290                 295                 300

Ile Ile Gly Gly Gly Phe Leu Gly Ser Glu Leu Ala Cys Ala Leu Gly
305                 310                 315                 320

Arg Lys Ala Arg Ala Leu Gly Thr Glu Val Ile Gln Leu Phe Pro Glu
                325                 330                 335

Lys Gly Asn Met Gly Lys Ile Leu Pro Glu Tyr Leu Ser Asn Trp Thr
            340                 345                 350

Met Glu Lys Val Arg Arg Glu Gly Val Lys Val Met Pro Asn Ala Ile
        355                 360                 365

Val Gln Ser Val Gly Val Ser Ser Gly Lys Leu Leu Ile Lys Leu Lys
    370                 375                 380

Asp Gly Arg Lys Val Glu Thr Asp His Ile Val Ala Ala Val Gly Leu
385                 390                 395                 400

Glu Pro Asn Val Glu Leu Ala Lys Thr Gly Gly Leu Glu Ile Asp Ser
                405                 410                 415
```

-continued

```
Asp Phe Gly Gly Phe Arg Val Asn Ala Glu Leu Gln Ala Arg Ser Asn
            420                 425                 430

Ile Trp Val Ala Gly Asp Ala Ala Cys Phe Tyr Asp Ile Lys Leu Gly
        435                 440                 445

Arg Arg Arg Val Glu His His Asp His Ala Val Val Ser Gly Arg Leu
    450                 455                 460

Ala Gly Glu Asn Met Thr Gly Ala Ala Lys Pro Tyr Trp His Gln Ser
465                 470                 475                 480

Met Phe Trp Ser Asp Leu Gly Pro Asp Val Gly Tyr Glu Ala Ile Gly
                485                 490                 495

Leu Val Asp Ser Ser Leu Pro Thr Val Gly Val Phe Ala Lys Ala Thr
            500                 505                 510

Ala Gln Asp Asn Pro Lys Ser Ala Thr Glu Gln Ser Gly Thr Gly Ile
        515                 520                 525

Arg Ser Glu Ser Glu Thr Glu Ser Glu Ala Ser Glu Ile Thr Ile Pro
    530                 535                 540

Pro Ser Thr Pro Ala Val Pro Gln Ala Pro Val Gln Gly Glu Asp Tyr
545                 550                 555                 560

Gly Lys Gly Val Ile Phe Tyr Leu Arg Asp Lys Val Val Val Gly Ile
                565                 570                 575

Val Leu Trp Asn Ile Phe Asn Arg Met Pro Ile Ala Arg Lys Ile Ile
            580                 585                 590

Lys Asp Gly Glu Gln His Glu Asp Leu Asn Glu Val Ala Lys Leu Phe
        595                 600                 605

Asn Ile His Glu Asp
    610


<210> SEQ ID NO 2
<211> LENGTH: 142
<212> TYPE: PRT
<213> ORGANISM: Homo sapiens

<400> SEQUENCE: 2

Met Ser Tyr Cys Arg Gln Glu Gly Lys Asp Arg Ile Ile Phe Val Thr
1               5                   10                  15

Lys Glu Asp His Glu Thr Pro Ser Ser Ala Glu Leu Val Ala Asp Asp
            20                  25                  30

Pro Asn Asp Pro Tyr Glu Glu His Gly Leu Ile Leu Pro Asn Gly Asn
        35                  40                  45

Ile Asn Trp Asn Cys Pro Cys Leu Gly Gly Met Ala Ser Gly Pro Cys
    50                  55                  60

Gly Glu Gln Phe Lys Ser Ala Phe Ser Cys Phe His Tyr Ser Thr Glu
65                  70                  75                  80

Glu Ile Lys Gly Ser Asp Cys Val Asp Gln Phe Arg Ala Met Gln Glu
                85                  90                  95

Cys Met Gln Lys Tyr Pro Asp Leu Tyr Pro Gln Glu Asp Glu Asp Glu
            100                 105                 110

Glu Glu Glu Arg Glu Lys Lys Pro Ala Glu Gln Ala Glu Glu Thr Ala
        115                 120                 125

Pro Ile Glu Ala Thr Ala Thr Lys Glu Glu Glu Gly Ser Ser
    130                 135                 140


<210> SEQ ID NO 3
<211> LENGTH: 511
<212> TYPE: PRT
```

```
<213> ORGANISM: artificial
<220> FEATURE:
<223> OTHER INFORMATION: AIF 103-613

<400> SEQUENCE: 3

Gly Leu Thr Pro Glu Gln Lys Gln Lys Lys Ala Ala Leu Ser Ala Ser
1               5                   10                  15

Glu Gly Glu Glu Val Pro Gln Asp Lys Ala Pro Ser His Val Pro Phe
            20                  25                  30

Leu Leu Ile Gly Gly Gly Thr Ala Ala Phe Ala Ala Ala Arg Ser Ile
        35                  40                  45

Arg Ala Arg Asp Pro Gly Ala Arg Val Leu Ile Val Ser Glu Asp Pro
    50                  55                  60

Glu Leu Pro Tyr Met Arg Pro Pro Leu Ser Lys Glu Leu Trp Phe Ser
65                  70                  75                  80

Asp Asp Pro Asn Val Thr Lys Thr Leu Arg Phe Lys Gln Trp Asn Gly
                85                  90                  95

Lys Glu Arg Ser Ile Tyr Phe Gln Pro Pro Ser Phe Tyr Val Ser Ala
            100                 105                 110

Gln Asp Leu Pro His Ile Glu Asn Gly Gly Val Ala Val Leu Thr Gly
        115                 120                 125

Lys Lys Val Val Gln Leu Asp Val Arg Asp Asn Met Val Lys Leu Asn
    130                 135                 140

Asp Gly Ser Gln Ile Thr Tyr Glu Lys Cys Leu Ile Ala Thr Gly Gly
145                 150                 155                 160

Thr Pro Arg Ser Leu Ser Ala Ile Asp Arg Ala Gly Ala Glu Val Lys
                165                 170                 175

Ser Arg Thr Thr Leu Phe Arg Lys Ile Gly Asp Phe Arg Ser Leu Glu
            180                 185                 190

Lys Ile Ser Arg Glu Val Lys Ser Ile Thr Ile Ile Gly Gly Gly Phe
        195                 200                 205

Leu Gly Ser Glu Leu Ala Cys Ala Leu Gly Arg Lys Ala Arg Ala Leu
    210                 215                 220

Gly Thr Glu Val Ile Gln Leu Phe Pro Glu Lys Gly Asn Met Gly Lys
225                 230                 235                 240

Ile Leu Pro Glu Tyr Leu Ser Asn Trp Thr Met Glu Lys Val Arg Arg
                245                 250                 255

Glu Gly Val Lys Val Met Pro Asn Ala Ile Val Gln Ser Val Gly Val
            260                 265                 270

Ser Ser Gly Lys Leu Leu Ile Lys Leu Lys Asp Gly Arg Lys Val Glu
        275                 280                 285

Thr Asp His Ile Val Ala Ala Val Gly Leu Glu Pro Asn Val Glu Leu
    290                 295                 300

Ala Lys Thr Gly Gly Leu Glu Ile Asp Ser Asp Phe Gly Gly Phe Arg
305                 310                 315                 320

Val Asn Ala Glu Leu Gln Ala Arg Ser Asn Ile Trp Val Ala Gly Asp
                325                 330                 335

Ala Ala Cys Phe Tyr Asp Ile Lys Leu Gly Arg Arg Arg Val Glu His
            340                 345                 350

His Asp His Ala Val Val Ser Gly Arg Leu Ala Gly Glu Asn Met Thr
        355                 360                 365

Gly Ala Ala Lys Pro Tyr Trp His Gln Ser Met Phe Trp Ser Asp Leu
    370                 375                 380

Gly Pro Asp Val Gly Tyr Glu Ala Ile Gly Leu Val Asp Ser Ser Leu
```

-continued

```
385                 390                 395                 400

Pro Thr Val Gly Val Phe Ala Lys Ala Thr Ala Gln Asp Asn Pro Lys
                405                 410                 415

Ser Ala Thr Glu Gln Ser Gly Thr Gly Ile Arg Ser Glu Ser Glu Thr
            420                 425                 430

Glu Ser Glu Ala Ser Glu Ile Thr Ile Pro Pro Ser Thr Pro Ala Val
        435                 440                 445

Pro Gln Ala Pro Val Gln Gly Glu Asp Tyr Gly Lys Gly Val Ile Phe
    450                 455                 460

Tyr Leu Arg Asp Lys Val Val Val Gly Ile Val Leu Trp Asn Ile Phe
465                 470                 475                 480

Asn Arg Met Pro Ile Ala Arg Lys Ile Ile Lys Asp Gly Glu Gln His
                485                 490                 495

Glu Asp Leu Asn Glu Val Ala Lys Leu Phe Asn Ile His Glu Asp
            500                 505                 510


<210> SEQ ID NO 4
<211> LENGTH: 27
<212> TYPE: PRT
<213> ORGANISM: artificial
<220> FEATURE:
<223> OTHER INFORMATION: peptide N27

<400> SEQUENCE: 4

Met Ser Tyr Cys Arg Gln Glu Gly Lys Asp Arg Ile Ile Phe Val Thr
1               5                   10                  15

Lys Glu Asp His Glu Thr Pro Ser Ser Ala Glu
            20                  25
```